US00PP27805P3

(12) United States Plant Patent
van der Zwet

(10) Patent No.: US PP27,805 P3
(45) Date of Patent: Mar. 21, 2017

(54) ***CAMPANULA* PLANT NAMED 'CHANTAL'**

(50) Latin Name: *Campanula glomerata*
Varietal Denomination: Chantal

(71) Applicant: Alexius Joannes Joseph van der Zwet, Oude-Wetering (NL)

(72) Inventor: Alexius Joannes Joseph van der Zwet, Oude-Wetering (NL)

(73) Assignee: Green Elite Collection B.V., Lisserbroek (NL)

( * ) Notice: Subject to any disclaimer, the term of this patent is extended or adjusted under 35 U.S.C. 154(b) by 0 days.

(21) Appl. No.: 14/756,082

(22) Filed: Jul. 29, 2015

(65) Prior Publication Data

US 2017/0034978 P1 Feb. 2, 2017

(51) Int. Cl.
*A01H 5/02* (2006.01)

(52) U.S. Cl.
USPC ..... Plt./414

(58) Field of Classification Search
USPC ..... Plt./414
See application file for complete search history.

*Primary Examiner* — Anne Grunberg
(74) *Attorney, Agent, or Firm* — C. A. Whealy

(57) ABSTRACT

A new and distinct *Campanula* plant named 'Chantal', characterized by its compact and upright plant habit; strong stems; freely flowering habit; light purple-colored flowers that have fused petal apices; and relatively long flowering period.

3 Drawing Sheets

Botanical designation: *Campanula glomerata.*
Cultivar denomination: 'CHANTAL'.

CROSS-REFERENCED TO CLOSELY-RELATED APPLICATION

Title: *Campanula* Plant Named 'Chico Lila'.
Applicant: Alexius Joannes Joseph van der Zwet
Filed: Concurrently with this application having application Ser. No. 14/756,086

BACKGROUND OF THE INVENTION

The present invention relates to a new and distinct *Campanula* plant, botanically known as *Campanula glomerata* and hereinafter referred to by the cultivar name 'Chantal'.

The new *Campanula* plant is a product of a planned breeding program conducted by the Inventor in Oude-Wetering, The Netherlands. The objective of the breeding program is to create new freely-flowering *Campanula* plants that flower for a long period of time.

The new *Campanula* plant originated from an open-pollination during the summer of 2007 of an unnamed selection of *Campanula glomerata*, not patented, as the female, or seed, parent with an unknown selection of *Campanula glomerata*, as the male, or pollen, parent. The new *Campanula* plant was discovered and selected by the Inventor as a single flowering plant from within the progeny of the stated open-pollination grown in a controlled environment in Oude-Wetering, The Netherlands in June, 2009.

Asexual reproduction of the new *Campanula* plant by divisions a controlled environment in Oude-Wetering, The Netherlands, since August, 2009, has shown that the unique features of the new *Campanula* plant are stable and reproduced true to type in successive generations.

SUMMARY OF THE INVENTION

Plants of the new *Campanula* plant have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Chantal'. These characteristics in combination distinguish 'Chantal' as a new and distinct *Campanula* plant:

1. Compact and upright plant habit.
2. Strong stems.
3. Freely flowering habit.
4. Light purple-colored flowers that have fused petal apices.
5. Relatively long flowering period.

Plants of the new *Campanula* differ from plants of the female parent selection primarily in plant size as plants of the new *Campanula* are more compact than plants of the female parent selection.

Plants of the new *Campanula* differ from plants of 'Chico Lila', disclosed in a U.S. Plant Patent application filed concurrently having application Ser. No. 14/756,086, in the following characteristics:

1. Petals of flowers of plants of the new *Campanula* are fused at the apices whereas petals of flowers of plants of 'Chico Lila' are not fused at the apices.
2. Plants of the new *Campanula* and 'Chico Lila' differ in flower color as plants of 'Chico Lila' have lilac-colored flowers.

Plants of the new *Campanula* can be compared to plants of *Campanula glomerata* 'Emerald', disclosed in U.S. Plant Pat. No. 18,343. In side-by-side comparisons conducted by the Inventor in Oude-Wetering, The Netherlands, plants of the new *Campanula* differed primarily from plants of 'Emerald' in the following characteristics:

1. Plants of the new *Campanula* were more compact than plants of 'Emerald'.

2. Plants of the new *Campanula* had shorter and stronger stems than plants of 'Emerald'.
3. Petals of flowers of plants of the new *Campanula* were fused at the apices whereas petals of flowers of plants of 'Emerald' were not fused at the apices.
4. Plants of the new *Campanula* and 'Emerald' differed in flower color as plants of 'Emerald' had light purple-colored flowers with darker purple-colored apices.

Plants of the new *Campanula* can also be compared to plants of *Campanula* 'Caroline', not patented. In side-by-side comparisons conducted by the Inventor in Oude-Wetering, The Netherlands, plants of the new *Campanula* differed primarily from plants of 'Caroline' in the following characteristics:

1. Plants of the new *Campanula* were more compact than plants of 'Caroline'.
2. Plants of the new *Campanula* had shorter and stronger stems than plants of 'Caroline'.
3. Petals of flowers of plants of the new *Campanula* were fused at the apices whereas petals of flowers of plants of 'Caroline' were not fused at the apices.
4. Plants of the new *Campanula* and 'Caroline' differed in flower color as plants of 'Caroline' had pinkish purple-colored flowers.

BRIEF DESCRIPTION OF THE PHOTOGRAPHS

The accompanying colored photographs illustrate the overall appearance of the new *Campanula* plant showing the colors as true as it is reasonably possible to obtain in colored reproductions of this type. Colors in the photographs may differ slightly from the color values cited in the detailed botanical description which accurately describe the actual colors of the new *Campanula* plant.

The photograph on the first sheet is a side perspective view of a typical flowering plant of 'Chantal' grown in a container.

The photograph on the second sheet is a close-up view of typical stems and leaves of 'Chantal'.

The photograph on the third sheet is a close-up view of typical inflorescences of 'Chantal'.

DETAILED BOTANICAL DESCRIPTION

Plants used for the aforementioned photographs and following description were grown in 24-cm containers during the spring in a glass-covered greenhouse in Oude-Wetering, The Netherlands and under cultural practices typical of commercial *Campanula* production. During the production of the plants, day temperatures ranged from 13° C. to 27° C. and night temperatures ranged from 5° C. to 18° C. Plants were one year old when the photographs and description were taken. In the following description, color references are made to The Royal Horticultural Society Colour Chart, 2007 Edition, except where general terms of ordinary dictionary significance are used.

Botanical classification: *Campanula glomerata* 'Chantal'.

Parentage:

*Female parent*.—Unnamed selection of *Campanula glomerata*, not patented.

*Male parent*.—Unknown selection of *Campanula glomerata*, not patented.

Propagation:

*Type*.—By divisions.

*Root description*.—Medium in thickness, fibrous; typically white in color, actual color of the roots is dependent on substrate composition, water quality, fertilizers, substrate temperature and physiological age of roots.

*Rooting habit*.—Freely branching; dense.

Plant description:

*Plant and growth habit*.—Herbaceous perennial; compact and upright plant form; inverted triangle; moderately vigorous growth habit; campanulate flowers arranged in terminal and axillary clusters.

*Plant height*.—About 41.3 cm.

*Plant width*.—About 28.6 cm.

*Branch description*.—Branching habit: Basal branching habit with about four basal branches and numerous basal branches developing per plant in subsequent years of growth. Length: About 32.6 cm. Diameter: About 8 mm. Internode length: About 1.8 cm. Strength: Strong. Aspect: Upright to about 15° from vertical. Texture: Densely pubescent. Luster: Slightly glossy. Color: Close to 147D strongly tinged with close to 183C.

Leaf description:

*Arrangement*.—Alternate, simple.

*Length*.—About 7.8 cm.

*Width*.—About 3.4 cm.

*Shape*.—Ovate.

*Apex*.—Acute.

*Base*.—Truncate or cordate.

*Margin*.—Finely serrate.

*Texture, upper and lower surfaces*.—Moderately rugose, rough; moderately pubescent.

*Luster, upper and lower surfaces*.—Slightly glossy.

*Venation pattern*.—Pinnate.

*Color*.—Developing leaves, upper surface: Close to between 137C and 138A. Developing leaves, lower surface: Close to 146B. Fully expanded leaves, upper surface: Close to 137B; venation, close to 143C. Fully expanded leaves, lower surface: Close to 137D; venation, close to 147D.

*Petioles*.—Stem leaves are sessile; basal leaves are petiolate. Length: About 7.4 cm. Diameter: About 2.5 mm. Strength: Strong. Texture, upper and lower surfaces: Pubescent. Color, upper and lower surfaces: Close to 146C to 146D moderately tinged with close to 183D.

Flower description:

*Flower arrangement and flowering habit*.—Single campanulate flowers arranged in terminal and axillary clusters; flowers face mostly upright to slightly outwardly; freely flowering habit with about 52 flowers developing in terminal clusters and about eleven flowers developing in axillary clusters; petals fused at the apex.

*Natural flowering season*.—Plants begin flowering about nine months after planting; relatively long flowering period, plants flower continuously from mid-June to early August in The Netherlands.

*Flower longevity on the plant*.—About ten days; flowers persistent.

*Fragrance*.—None detected.

*Flower buds*.—Length: About 3 cm. Diameter: About 1.4 cm. Shape: Narrowly oblong. Color: Proximally, close to 145D; distally, close to between N77B and N77D.

*Flower cluster height*.—About 5.7 cm.

*Flower cluster diameter*.—About 7.6 cm.

*Flower diameter*.—About 2 cm.

*Flower depth* (*height*).—About 4.2 cm.

*Petals*.—Quantity and arrangement: Typically five in a single whorl; fused toward the lower half of the petal and fused at the apex. Length: About 4.1 cm. Width: About 1.1 cm. Shape: Oblong to narrowly obovate; inverted carinate. Apex: Acute, fused. Margin: Entire. Texture, upper and lower surfaces: Smooth, glabrous. Luster, upper and lower surfaces: Slightly glossy. Color: When opening, upper surface: Close to 84D and 85D; towards the apex, close to 84B; at the apex, close to 146C. When opening, lower surface: Close to 84D; towards the apex, close to 84C; at the apex, close to 146C. Fully opened, upper and lower surfaces: Close to 84D; towards the apex, close to 84C; at the apex, close to 146C; color does not fade with development.

*Sepals*.—Quantity and arrangement: Typically five in a single whorl; fused towards the base. Length: About 1.8 cm. Width: About 3 mm. Shape: Lanceolate. Apex: Narrowly acute. Margin: Entire. Texture, upper surface: Smooth, glabrous; at the margins, moderately to densely pubescent. Texture, lower surface: Moderately to densely pubescent. Luster, upper and lower surfaces: Matte. Color: When opening, upper surface: Close to 143B to 143C; towards the apex, close to N137A. When opening, lower surface: Close to 143B; towards the apex, close to N137A. Fully opened, upper surface: Close to 143B to 143C; towards the apex, close to N137A. Fully opened, lower surface: Close to 143C; towards the apex, close to N137A.

*Peduncles*.—Length: About 2.2 cm. Diameter: About 6 mm. Aspect, flowers in terminal clusters: Mostly upright. Aspect, flowers in axillary clusters: About 30° from branch axis. Strength: Strong. Texture: Smooth, glabrous. Color: Close to 147D strongly tinged with close to 183C.

*Reproductive organs*.—Stamens: Quantity per flower: Five. Filament length: About 2 mm. Filament color: Close to NN155D. Anther shape: Lanceolate. Anther length: About 8 mm. Anther color: Close to 13A. Pollen amount: Scarce. Pollen color: Close to 4D. Pistils: Quantity per flower: One. Pistil length: About 2.2 cm. Stigma shape: Three-parted, decurrent. Stigma color: Close to 145A. Style length: About 2 cm. Style color: Close to 85B to 85C. Ovary color: Close to 145A to 145B.

*Seeds and fruits*.—Seed and fruit production has not been observed on plants of the new *Campanula*.

Disease & pest resistance: Plants of the new *Campanula* have not been noted to be resistant to pathogens and pests common to *Campanula* plants.

Garden performance: Plants of the new *Campanula* have exhibited good tolerance to rain and wind, to tolerate high temperatures about 35° C. and to be suitable for USDA Hardiness Zones 3 through 8.

It is claimed:

1. A new and distinct *Campanula* plant named 'Chantal' as illustrated and described.

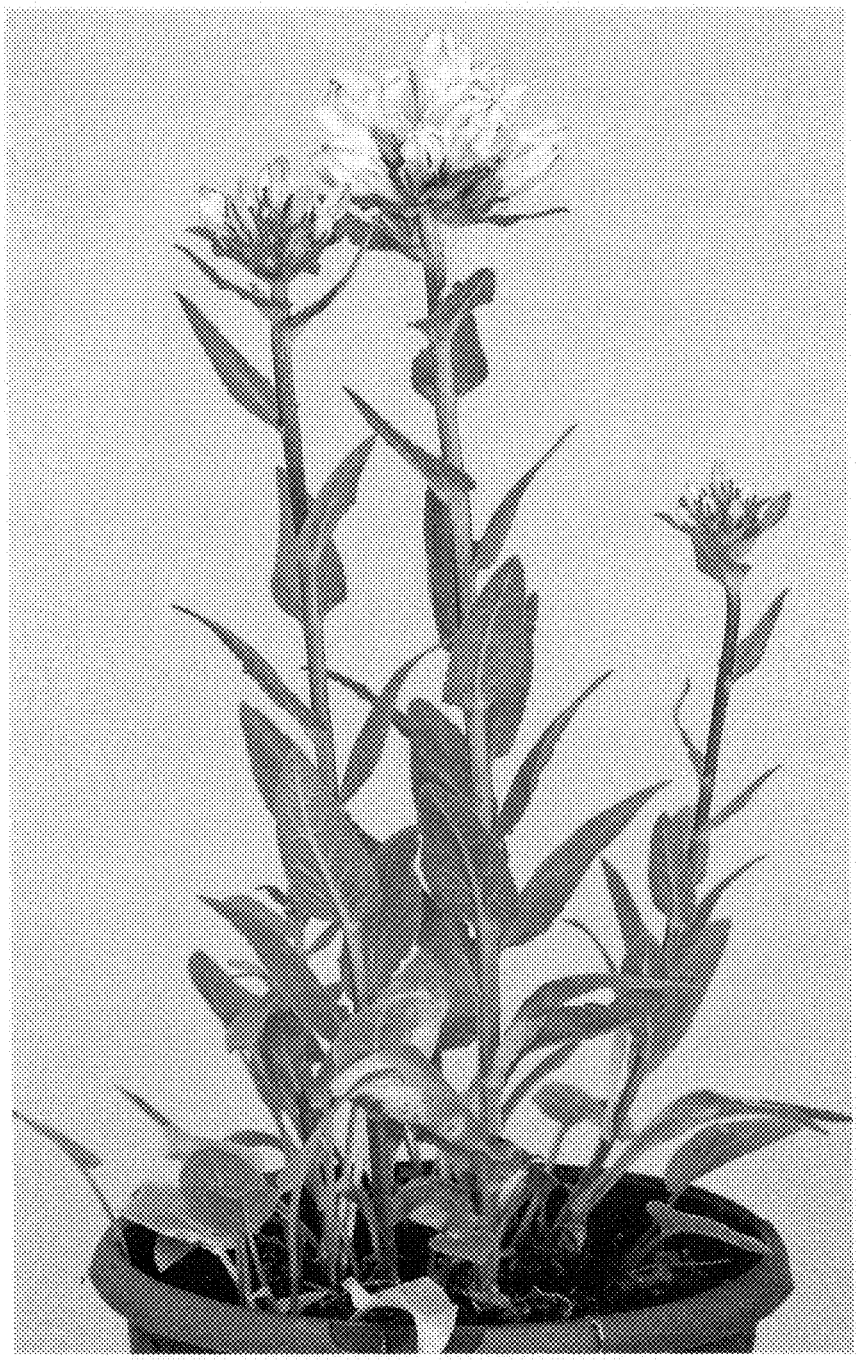

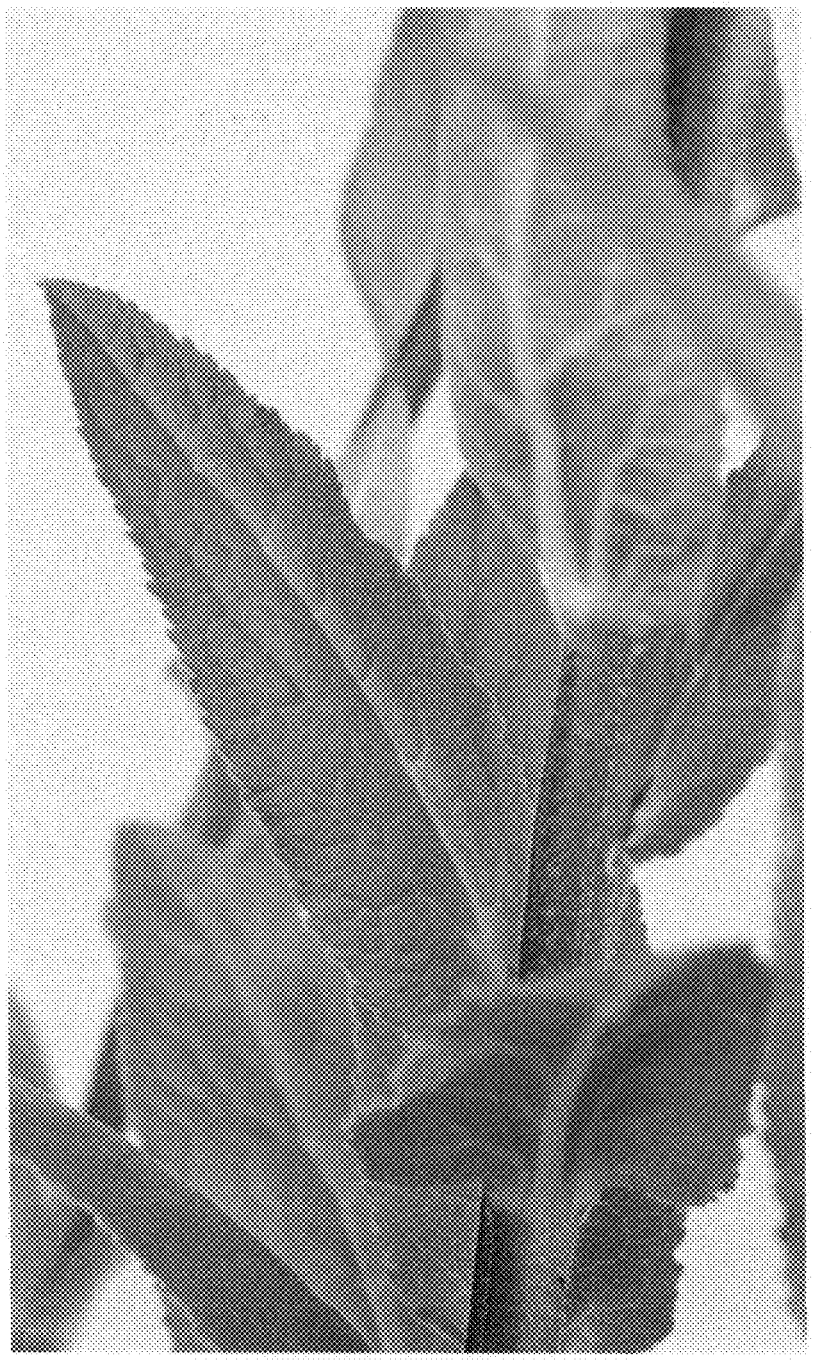

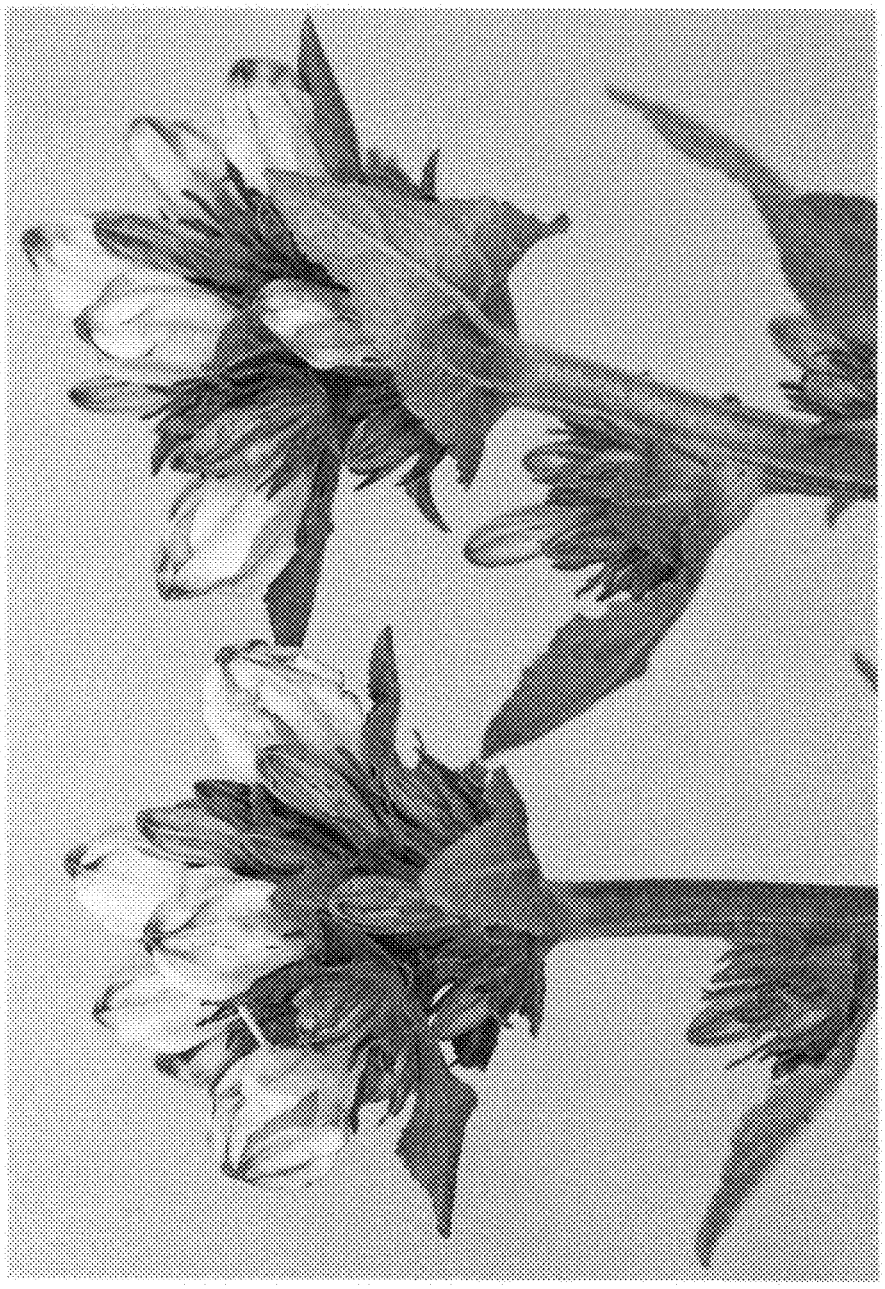

* * * * *